United States Patent [19]

Hilty et al.

[11] Patent Number: 5,922,344
[45] Date of Patent: *Jul. 13, 1999

[54] PRODUCT FOR PREVENTION OF RESPIRATORY VIRUS INFECTION AND METHOD OF USE

[75] Inventors: Milo Duane Hilty, Lewis Center; Steven Neal Anderson; Joseph Paul Schaller, both of Columbus; Jin-Zhou Liu, Gahanna, all of Ohio

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/386,576

[22] Filed: Feb. 10, 1995

[51] Int. Cl.$^6$ ..................................................... A61K 47/32
[52] U.S. Cl. ............................................................. 424/439
[58] Field of Search ............................. 424/439; 426/801, 426/335

[56] References Cited

U.S. PATENT DOCUMENTS

| | | | |
|---|---|---|---|
| 3,911,108 | 10/1975 | Singh | 424/335 |
| 4,800,078 | 1/1989 | Prince et al. | 424/86 |
| 5,066,491 | 11/1991 | Stott et al. | |
| 5,290,540 | 3/1994 | Prince et al. | 424/45 |

FOREIGN PATENT DOCUMENTS

| | | |
|---|---|---|
| 2040770 | 4/1991 | Canada . |
| 06345668 | 6/1993 | Japan . |
| 9201473 | 2/1992 | WIPO . |
| 9219244 | 11/1992 | WIPO . |
| 9417105 | 8/1994 | WIPO . |

OTHER PUBLICATIONS

Ryan, Sherris Medical Microbiology, 3d ed., Appleton and Lange, p. 458, 1994.

Loegreid et al., "Neutralizing Activity in Human Milk Fractions Against Respiratory Syncytial Virus", Acta Paediatrica Scandinavia, 75: 696–701, 1986.

Okamoto et al., "Antiviral Factors in Human Milk: Implications in Respiratory Syncytial Virus Infection", Acta Paediatrica Scandinavica Supplement 351: 137–143, 1989.

Piedra et al., "Mechanism of Lung Inpey in Cotton Rats Immunized with Formalin–Inactivated Respiratory Syncytial Virus", Vaccine 7:34–38, 1989.

Piazza et al., "Immunotherapy of Respiratory Syncytial Virus Infection in Cotton Rats (*Sigmodum fulnevents*) Using IgG in a Small–Particle Aerosol," The Journal of Infectious Diseases 166:1422–4, 1992.

Prince et al., "The Pathogenesis of Respiratory Syncytial Virus in Cotton Rats," American Journal of Pathology 93(3): 1978, 771–783.

*Primary Examiner*—Carlos Azpuru
*Attorney, Agent, or Firm*—Donald O. Nickey; Thomas D. Brainard

[57] ABSTRACT

A method of treating pneumonia or other respiratory disease caused by respiratory syncytial virus, adenovirus, parainfluenza virus, or influenza virus by orally administering a liquid, preferably an infant formula, containing a virus neutralizing antibody.

19 Claims, No Drawings

PRODUCT FOR PREVENTION OF RESPIRATORY VIRUS INFECTION AND METHOD OF USE

BACKGROUND OF THE INVENTION

1. Field of the Invention

This invention relates to an orally administered antibody with respiratory syncytial virus (RSV), adenovirus, parainfluenza virus, or influenza virus neutralization activity and its use to decrease the incidence or severity of RSV or other viral infections of the upper and lower respiratory tract.

2. Description of the Prior Art

Respiratory syncytial virus is the major cause of pneumonia and bronchiolitis in infancy. Infants between the ages of two and five months have the most severe disease and may require hospitalization. More than half of all infants become infected with RSV during their first year of exposure, and nearly all are infected after a second year. Children who attend day care centers tend to have more severe infections and at an earlier age. Repeated RSV infections are common, although repeat episodes tend to be less severe.

During seasonal epidemics most infants, children, and adults are at risk for infection or reinfection. In addition to infections in healthy infants and children, other groups at risk for serious RSV infections include premature infants, hospitalized children, infants and children with cardiac or pulmonary disorders, immune compromised children and adults, and the elderly. Symptoms of RSV infection range from a mild cold to severe bronchiolitis and pneumonia. Respiratory syncytial virus has also been associated with acute otitis media and RSV can be recovered from middle ear fluid.

Respiratory syncytial virus is an RNA virus that can produce cell fusion (syncytia) in tissue culture. It is classified as a pneumovirus within the paramyxovirus family. The RNA genome codes for at least 10 proteins including two matrix proteins in the viral envelope (Ryan, *Sherris' Medical Microbiology*, 3d ed., Appleton and Lange, p. 458, 1994). One matrix protein forms the inner lining of the viral envelope. Antigens on the surface of the envelope are the G glycoprotein, the probable attachment site to host cell receptors, and the F glycoprotein that induces fusion. G glycoprotein antibodies can neutralize the virus in vitro.

Infection with the virus causes both IgG and IgA humoral and secretory antibody responses. Immunity is not permanent and repeated infections are common, however the severity of illness tends to diminish with increasing age and with successive reinfection. No vaccine has been shown to be protective against RSV and antiviral drugs have so far had only limited utility. Breast feeding may offer some protection against RSV infection. RSV-specific IgA and IgG antibodies have been found in human milk and colostrum and RSV neutralization can be accomplished in cell culture with both immunoglobulin and non-immunoglobulin components of human milk (Laegreid et al., "Neutralizing Activity in Human Milk Fractions against Respiratory Syncytial Virus, *Acta Paediatrica Scandinavica*, 75:696–701, 1986).

Okamato et al., (*Acta Paediatrica Scandinavica Supplement*, 351:137–143, 1989) report that immunity acquired by an infant either through the placenta or through breast feeding may reduce the risk of lower respiratory tract disease. The focus of the report of Okamato et al. is on the role of maternal antibodies transmitted in breast milk and the possible role of breast milk in modulating an infant's immune response to RSV. The focus of the instant invention is on a method of producing passive immunity by adding neutralizing antibodies to a product that will be orally ingested. Orally ingested as used herein refers to a substance that is swallowed by the host.

Previous treatments for infection by RSV have relied upon either parenteral or aerosol administration of agents such as monoclonal antibodies or viricidal drugs such as ribavirin. The present invention discloses oral administration of an antibody with RSV neutralizing activity.

Prince et al. (U.S. Pat. No. 4,800,078) teach a method for topical application of antibodies to RSV into the lower respiratory tract, preferably by administering immunoglobulins as small particle aerosol. The immunoglobulins can also be administered by the intravenous route.

In U.S. Pat. No. 5,290,540, Prince et al. disclose topical administration in the form of small particle aerosol of both an anti-inflammatory agent and an anti-infectious agent in the treatment of pneumonia caused by bacteria or viruses including RSV.

CA 2,040,770 to Young et al. discloses a process for the treatment of respiratory viruses, including RSV, by administering a neutralizing or non-neutralizing monoclonal antibody against a fusion protein of RSV (the F glycoprotein). Monoclonal antibody treatment using the method of Young et al. may be topical and administered intranasally or by breathing an aerosol, or systemic by intramuscular administration. The present invention, by contrast, discloses an orally administered treatment.

WO 92/01473 discloses the treatment of lower respiratory tract viral disease using the small particle aerosol method to deliver neutralizing and/or therapeutic monoclonal antibodies to specific viral surface antigenic sites.

WO 92/19244 teaches the combination of an anti-infective agent such as human immunoglobulin G or an antibiotic combined with an anti-inflammatory agent or corticosteroid delivered into the respiratory tract in the form of small particle aerosol.

WO 94/17105 discloses human-murine chimeric antibodies with high specific neutralizing activity against RSV, preferably against the RSV F antigen.

The prior art references disclose delivery of a virus neutralizing compound either topically by inhalation of a small particle aerosol or parenterally by intravenous or intramuscular injection. Feeding a non-absorbed RSV neutralizing compound to prevent or decrease the incidence and severity of RSV infection has not been disclosed or demonstrated in the prior art references. This concept, as demonstrated in the present invention, depends on the ability of an RSV neutralizing antibody to decrease the viral load on mucosal surfaces of the nasopharynx, oropharynx, and hypopharynx, and thereby prevent or decrease the spread of infectious virus from nose to lung when the antibody is swallowed. Delivery of an RSV neutralizing antibody in a liquid product is particularly advantageous because of the ease of administration.

DESCRIPTION OF THE INVENTION

The invention is an orally administered liquid product containing a respiratory virus neutralizing antibody. In one embodiment of the invention the respiratory virus neutralizing antibody is added to a nutritional product. The invention is also a method for delivering an effective concentration of the respiratory virus neutralizing antibody by adding it to a liquid product. As used herein and in the claims a respiratory neutralizing antibody is understood to mean antibody from any mammalian source such as human or bovine that can neutralize respiratory virus. In one embodiment of the invention the respiratory virus neutralizing antibody is added to a nutritional product for infants, such as infant formula, and is fed to the infant during the first year of life. The infant formulation could be a powder for reconstitution with water, a ready-to-feed liquid or a concentrated liquid. Respiratory viruses to which the invention is applicable include respiratory syncytial virus, adenovirus, parainfluenza virus, and influenza virus.

Experimental Protocol

Studies will be undertaken to determine the impact of feeding neutralizing antibodies against human respiratory syncytial virus (HRSV) induced pulmonary infection in animals. Objectives of the studies include identification of an animal model for nasal challenge with HRSV in order to evaluate the influence of dietary feeding on HRSV pulmonary infection; and determination whether feeding HRSV neutralizing antibody and/or other neutralizing compounds can prevent or mitigate pulmonary infection in the animal following nasal challenge with HRSV. A positive outcome with an animal model will eventually permit clinical evaluation of a liquid product enhanced with an HRSV neutralizing compound.

Animals and diet: Thirty day old inbred cotton rats (Sigmodon fulviventer) free of serum neutralizing antibody against human respiratory syncytial virus (HRSV) will be used. The rats are to be fed a basal liquid diet consisting of infant formula for two days before experiments begin. One day before intranasal inoculation of virus the experimental diets will be provided. Food intake and body weight change are to be monitored daily. Upon completion of the study, all rats will be killed by carbon dioxide asphyxiation and nasal and lung tissue will be removed for analysis.

Virus: The virus to be used is human respiratory syncytial virus subgroup A2 (HRSV/Long). The virus will be prepared by infecting monolayers of HEp-2 cells, which will be grown until the monolayers show approximately 9-% syncytia formation. The medium from the monolayers will be collected, pooled and clarified by centrifugation at 450×g. Clarified supernatant fluid will be passed through a 0.45 $\mu$M filter. This supernatant will contain human respiratory syncytial virus (HRSV) at 106 PFU/ml as determined by plaque assay.

Antibodies: Polyclonal HRSV antibodies (HRSVIG) obtained commercially (Sandoz, East Hanover, N.J.) will be incorporated into liquid diets at varied concentrations and the in vitro neutralizing activity of the experimental diets supplemented with HRSVIG will be determined by plaque reduction assay.

Virus titration: Oropharyngeal swabs will be taken daily before 8 a.m. from the second day of virus inoculation until the end of the experiment. HRSV antigen in all swabs will be determined. At necropsy, nasal and lung tissue will be homogenized in 10 parts (wt/vol) of Hanks balanced salt solution supplemented with 0.218 M sucrose, 4.4 mM glutamate, 3.8 mM $KH_2PO_4$, 3.2 mM $K_2HPO_4$. The resulting suspension will be used to determine virus titers by plaque assay on Hep-2 cell monolayers.

Histopathologic examination: Formalin-fixed nasal tissues and lungs will be embedded in paraffin, cut into coronal sections, stained with hematoxylineosin with periodic acid-Schiff (PAS), and examined under a light microscope. Slides will be prepared by a pathologist for whom sample numbers will be blind during microscopic examination. Histopathology of the lung stained by PAS will be scored from 0–2.0, 2.1–6.0, 6.1–10.0, 10.1–12 as defined by Piedra et al. ("Mechanism of lung injury in cotton rats immunized with formalin-inactivated respiratory syncytial virus", *Vaccine* 7:34–38, 1989).

Statistical analysis: Single-tail $X^2$ will be used to compare proportions of the measurements between independent groups. Analysis of variance will be used to compare virus titers and severity of lung injury.

Example: Study to examine the dose-response relationship between dietary human respiratory syncytial virus immunoglobulin (HRSVIG) and human respiratory syncytial virus (HRSV) infection Piazza et al. ("Immunotherapy of respiratory syncytial virus infection in cotton rats (Sigmodon fulviventer) using IgG in a small-particle aerosol", *Journal of Infectious Disease* 166:1422–1424, 1992) have shown that HRSVIG at 5 mg/100 ml solution, administered for 15 minutes in a small-particle aerosol three days after intranasal inoculation of cotton rats with HRSV, reduced virus titer 50-fold. The present study is designed to determine whether oral administration of HRSVIG can similarly reduce pulmonary infection. This will be done by incorporating an anti-RSV IgG into a liquid diet at various concentrations, after which the in vitro neutralizing activity of the experimental diets will be determined with the plaque reduction assay as described by Prince et al. ("The pathogenesis of respiratory syncytial virus infection in cotton rats", *American Journal of Pathology* 93:771–792, 1978).

For the study, 70 rats will be divided into 7 treatment groups. Treatment group 1 will comprise 10 rats and will serve as a negative control. They will be fed the basal liquid diet and inoculated with 0.1 ml of supernatant from HEp-2 cell culture medium which lacks cells or HRSV. Ten rats in each of treatment groups 2, 3, 4, and 5 will be fed the basal liquid diet supplemented with HRSVIG at 0, 0.5, 5, and 10 mg/100 ml respectively. Assuming that each rat will consume 100 ml of liquid diet, the anticipated daily dose for rats in each group should be 0, 0.5, 5, and 10 mg HRSVIG. Rats in treatment groups 6 and 7 will be fed the basal liquid diet supplemented with other agents to be tested for anti-respiratory virus properties. One day after consuming the experimental diets, rats in treatment groups 2–7 will be inoculated intranasally with HRSV/Long using 0.1 ml of virus suspension containing HRSV at $10^3$ PFU/ml (plaque forming units). All rats will continue consuming their assigned diets until termination of the study. Four days after being challenged with the virus, all rats will be killed and nasal tissues and lungs will be removed for sequential analysis.

An effective concentration of the respiratory virus neutralizing antibody can be added to a liquid product. In a specific embodiment of the invention the liquid product is an infant formula that can be fed to an infant during the first year of life, the period when the infant is most vulnerable to RSV infection. Infant nutritional formulations could be in powder form for reconstitution with water, a ready-to-feed liquid, or a concentrated liquid. It should be understood, however, that the scope of the present invention is not to be limited to these specific embodiments. The invention may be practiced other than as particularly described and still be within the scope of the accompanying claims.

What is claimed is:

1. A method for preventing or treating respiratory virus infections of the upper and/or lower respiratory tract caused in a human by respiratory syncytial virus, which method comprises:
   a. adding a therapeutically effective amount of an antibody with respiratory syncytial virus neutralization activity selected from the group consisting of IgG, IgA, and mixtures thereof to a liquid nutritional product; and
   b. orally administering the liquid nutritional product to a human in need thereof.

2. A method for preventing or treating respiratory syncytial virus infections according to claim 1, wherein the antibody is IgG.

3. A method for preventing or treating respiratory syncytial virus infections according to claim 1, wherein the antibody is IgA.

4. A method for preventing or treating respiratory syncytial virus infections according to claim 1, wherein the liquid is infant formula.

5. An artificial liquid nutritional product for the prevention or treatment of respiratory syncytial virus infection comprising nutrients and a respiratory syncytial virus neutralizing antibody selected from the group consisting of IgG, IgA and mixtures thereof, in an amount effective to decrease the viral load of respiratory syncytial virus on mucosal surfaces when said nutritional product is orally administered in amounts appropriate to provide nutrition to a human.

6. An infant formula that comprises a therapeutically effective amount of a respiratory syncytial virus neutralizing antibody.

7. An infant formula according to claim 6, wherein said infant formula is in a liquid, ready to feed form.

8. An infant formula according to claim 6, wherein said infant formula is in a concentrated liquid form, for dilution prior to use.

9. An infant formula according to claim 6, wherein said infant formula is in a powder form, for reconstitution prior to use.

10. The method according to claim 1, comprising orally administering the liquid nutritional product to an infant or young child.

11. A method for preventing or treating infections of the upper and/or lower respiratory tract caused in a human by Respiratory Syncytial Virus (RSV), comprising orally administering to said human a liquid nutritional product having an antibody selected from the group consisting of IgG, IgA, and mixtures thereof, wherein said antibody exhibits RSV neutralizing activity, in an amount effective to decrease the viral load of RSV on mucosal surfaces.

12. The method according to claim 11, wherein the antibody comprises IgG.

13. The method according to claim 11, wherein the antibody comprises IgA.

14. The method according to claim 11, wherein the liquid nutritional product is an infant formula.

15. The method according to claim 14, comprising orally administering the infant formula to an infant or young child.

16. The method according to claim 11, wherein the viral load of RSV is decreased on a mucosal surface selected from the group consisting of nasopharynx, oropharynx, and hypopharynx.

17. A nutritional product according to claim 5, wherein said nutritional product is in a liquid, ready to feed form.

18. A nutritional product according to claim 5, wherein said nutritional product is in a concentrated liquid form, for dilution prior to use.

19. A nutritional product according to claim 5, wherein said nutritional product is in a powder form, for reconstitution prior to use.

* * * * *